United States Patent
Bigelow et al.

(10) Patent No.: US 12,428,609 B2
(45) Date of Patent: Sep. 30, 2025

(54) ORGANOLEPTIC COMPOUNDS

(71) Applicant: INTERNATIONAL FLAVORS & FRAGRANCES INC., Union Beach, NJ (US)

(72) Inventors: Penelope Bigelow, Union Beach, NJ (US); Clint Wermes, Tinton Falls, NJ (US); Robert Belko, Monroe, NJ (US); Richard A. Weiss, Livingston, NJ (US); Anubhav P. S. Narula, Hazlet, NJ (US); Michael Monteleone, Hazlet, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 582 days.

(21) Appl. No.: 17/779,580

(22) PCT Filed: Nov. 25, 2020

(86) PCT No.: PCT/US2020/062124
§ 371 (c)(1),
(2) Date: May 25, 2022

(87) PCT Pub. No.: WO2021/108472
PCT Pub. Date: Jun. 3, 2021

(65) Prior Publication Data
US 2023/0100090 A1      Mar. 30, 2023

Related U.S. Application Data

(60) Provisional application No. 62/940,967, filed on Nov. 27, 2019.

(51) Int. Cl.
| | |
|---|---|
| *C11D 3/12* | (2006.01) |
| *A61K 8/34* | (2006.01) |
| *A61Q 13/00* | (2006.01) |
| *C07C 47/263* | (2006.01) |
| *C11B 9/00* | (2006.01) |
| *C11D 3/20* | (2006.01) |
| *C11D 3/22* | (2006.01) |
| *C11D 3/37* | (2006.01) |
| *C11D 3/50* | (2006.01) |
| *C11D 9/44* | (2006.01) |

(52) U.S. Cl.
CPC ............. *C11D 3/2072* (2013.01); *A61K 8/34* (2013.01); *A61Q 13/00* (2013.01); *C07C 47/263* (2013.01); *C11B 9/0015* (2013.01); *C11D 3/50* (2013.01); *C11D 2111/12* (2024.01)

(58) Field of Classification Search
CPC ......... C11D 3/0047; C11D 3/044; C11D 3/12; C11D 3/20; C11D 3/22; C11D 3/37; C11D 3/50; C11D 9/44; A61K 8/34; A61Q 13/00; C11B 9/00
See application file for complete search history.

(56) References Cited

U.S. PATENT DOCUMENTS

2017/0327769 A1 * 11/2017 Goeke .................. C07C 47/263
2017/0362533 A1 * 12/2017 Baumgartner .......... C11B 9/003

FOREIGN PATENT DOCUMENTS

| JP | 52-91815 | * | 8/1977 | ............. C07C 47/26 |
| JP | 52091815 A | * | 8/1977 | ............. C07C 47/26 |

* cited by examiner

*Primary Examiner* — Brian P Mruk

(57) ABSTRACT

The present invention relates to novel compounds and their use as fragrance materials.

16 Claims, No Drawings

ORGANOLEPTIC COMPOUNDS

STATUS OF RELATED APPLICATION

This application is a 371 of International Application No. PCT/US2020/062124, filed Nov. 25, 2020, which claims priority to U.S. Provisional Patent Application No. 62/940,967, filed Nov. 27, 2019, the content of which is incorporated herein by reference in its entirety.

BACKGROUND

There is an ongoing need in the fragrance industry to provide new chemicals to give perfumers the ability to create new fragrances for perfumes, colognes and personal care products. Those with skill in the art appreciate how small differences in the chemical structure of the molecule can result in significant differences in the odor, notes and characteristics of a molecule. These variations and the ongoing need to discover and use the new chemicals in the development of new fragrances allow the perfumers to apply the new compounds in creating new fragrances.

SUMMARY OF THE INVENTION

The present invention provides novel compounds and their unexpected advantageous use in enhancing, improving or modifying the fragrance of perfumes, colognes, toilet water, fabric care products, personal products and the like.

More specifically, the present invention relates to novel hydroxy-4,8-dimethyl-dec-4-enal compounds represented by Formula I set forth below:

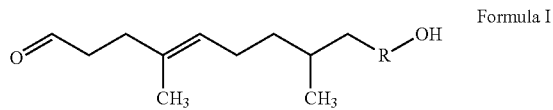

Formula I wherein R is a $C_1$-$C_3$ straight or branched alkylene group.

Another embodiment of the present invention relates to a subgenus of the above hydroxy-4,8-dimethyl-dec-4-enal compounds represented by Formula II set forth below:

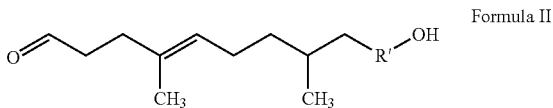

Formula II wherein R' is a $C_2$ or $C_3$ straight or branched alkylene group.

Other embodiments of the present invention relate to a fragrance formulation or fragrance product comprising the novel compounds provided.

Another embodiment of the present invention relates to a method of improving, enhancing or modifying a fragrance formulation comprising the step of adding to the fragrance formulation an olfactory acceptable amount of the novel compounds provided above.

These and other embodiments of the present invention will be apparent by reading the following specification.

DETAILED DESCRIPTION OF THE INVENTION

The hydroxy-4,8-dimethyl-dec-4-enal compounds represented by Formula I and II of the present invention are illustrated, for example, by following compounds presented in Table 1.

TABLE 1

| Structure No. | Compound |
|---|---|
| 1 | 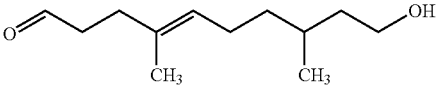<br>10-Hydroxy-4, 8-dimethyldec-4-enal |
| 2 | 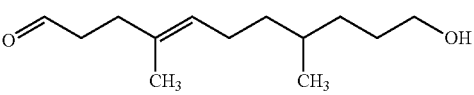<br>11-Hydroxy-4, 8-dimethylundec-4-enal |
| 3 | 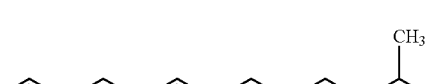<br>11-Hydroxy-4, 8-dimethyldodec-4-enal |
| 4 | 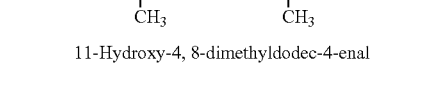<br>10-Hydroxy-4, 8-dimethylundec-4-enal |

Those with skill in the art will recognize that the compounds of the present invention may have a number of isomers such as positional isomers depending on the available starting materials. It is intended herein that the compounds described herein include isomeric mixtures as well as single isomers that may be separated using techniques known to those having skill in the art. Suitable techniques include chromatography such as high performance liquid chromatography, referred to as HPLC, and particularly silica gel chromatography and gas chromatography trapping known as GC trapping. Yet, commercial products are mostly offered as isomeric mixtures.

The preparation and isolation of the compounds of the present invention is detailed in the Examples. Materials were purchased from Sigma-Aldrich Corporation unless noted otherwise.

The compounds of the present invention exhibit floral, sweet juicy, green and watery lily of the valley notes, which are surprisingly and unexpectedly strong and long-lasting. The use of the compounds of the present invention is widely applicable in current perfumery products, including the preparation of perfumes and colognes, the perfuming of personal care products such as soaps, shower gels, and hair care products, fabric care products, air fresheners, and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like.

The nature and variety of the other ingredients that can also be employed are known to those with skill in the art. Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, *gardenia*, hawthorn, heliotrope, honeysuckle, hyacinth, jasmine, lilac, lily, *magnolia, mimosa, narcissus*, freshly-cut hay, orange blossom, orchid, *reseda*, sweet pea, trefle, tuberose, vanilla, violet, wallflower, and the like.

The term "alkyl" means a linear or branched saturated monovalent hydrocarbon, e.g., methyl, ethyl, propyl, 2-propyl, butyl (including all isomeric forms), pentyl (including all isomeric forms), hexyl (including all isomeric forms), and the like. The term "alkenyl" means a linear or branched unsaturated, aliphatic hydrocarbon containing at least one carbon-carbon double bond. The term "alkylene" refers to bivalent alkyl. Examples include —$CH_2$—, —$CH_2CH_2$—, —$CHCH_3$—, —$CH_2CH_2CH_2$—, —$CH_2$ ($CH_3$) $CH_2$—, —$CH_2CH_2CH_2CH_2$—, and the like.

The term "a buffering agent" as used herein is understood to mean, but not limited to, an acetate buffer, an alkylamine buffer, an aminoethyl alcohol buffer, an ammonium buffer, an arginine buffer, a barbiturate buffer, a borate buffer, a carbonate buffer, a citrate buffer, an ethylenediamine buffer, a gluconate (gluconolactone) buffer, a glutamate buffer, a glycine buffer, a glycyl glycine buffer, an imidazole buffer, a lactate buffer, a malate buffer, a phosphate buffer, a pyridine buffer, a tartrate buffer, a tris buffer, a triethanolamine buffer, and a mixture thereof. The buffering agent of the present invention maintains a desirable pH from about 5 to about 11 in a fragrance formulation.

The compounds of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), 4,4,10,10,11,12,12-heptamethyl-3-oxatricyclo [7.3.0.0<2,6>]dodecane (AMBER XTREME™), (3,3-dimethylcyclohexyl)ethyl ethyl propane-1,3-dioate (Applelide), (E/Z)-1-ethoxy-1-decene (Arctical), 2-ethyl-4-(2,2,3-trimethyl-3-cyclo-penten-1-yl)-2-buten-1-ol (Bacdanol), 2-methyl-3-[(1,7,7-trimethylbicyclo[2.2.1]hept-2-yl)oxy] exo-1-propanol (sold under the tradename BORNAFIX®), 1,2,3,5,6,7-hexahydro-1,1,2,3,3-pentamethyl-4H-inden-4-one (sold under the tradename CASHMERAN®), trimethylcyclopentenylmethyloxabicyclooctane (Cassiffix), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (sold under the tradename CYCLACET®), 3A,4,5,6,7,7A-hexahydro-4,7-methano-1H-inden-5/6-yl propinoate (sold under the tradename CYCLAPROP®), 3A, 4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (sold under the tradename HELIONAL®), 1-(2,6, 6-trimethyl-2-cyclohexen-1-yl)-1,6-heptadien-3-one (Hexalon), (Z)-3-hexenyl-2-hydroxybenzoate (Hexenyl Salicylate, CIS-3), 4-(2,6,6-trimethyl-2-cyclohexen-1-yl)-3-buten-2-one (Ionone a), 1-(1,2,3,4,5,6,7,8-octahydro-2,3,8, 8-tetramethyl-2-naphthalenyl)-ethan-1-one (sold under the tradename ISO E SUPER®), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (sold under the tradename KOAVONE®), 3/4-(4-hydroxy-4-methyl-pentyl) cyclohexene-1-carboxaldehyde (Lyral), 3-methyl-4-(2,6,6-trimethyl-2-cyclohexen-1-yl)-3-buten-2-one (Methyl Ionone y), 1-(2,6,6-trimethyl-2-cyclohexen-1-yl) pent-1-en-3-one (Methyl Ionone a Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo[7.4.0.0<2,6>]tridec-2(6)-ene (sold under the tradename NEBULONE®), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl) cyclohex-3-ene-1-carboxaldehyde (Precyclemone B), 4-methyl-8-methylene-2-adamantanol (Prismantol), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), 3-[cis-4-(2-methylpropyl)cyclohexyl]propanal (Starfleur), Terpineol, 2,4-dimethyl-3-cyclohexene-1-carboxaldehyde (sold under the tradename TRIPLAL®), decahydro-2,6,6,7,8,8-hexamethyl-2H-indeno[4,5-B]furan (Trisamber), 2-tert-butylcyclohexyl acetate (Verdox), (3E)-4-methyldec-3-en-5-one (Veridian), 4-tert-butylcyclohexyl acetate (Vertenex), acetyl cedrene (Vertofix), 3,6/4,6-dimethylcyclohex-3-ene-1-carboxaldehyde (Vertoliff) and (3Z)-1-[(2-methyl-2-propenyl)oxy]-3-hexene (Vivaldie).

The terms "fragrance formulation," "fragrance composition," "perfume formulation" and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising a compound of the present invention. Further, the fragrance formulation of the present invention comprises a compound of the present invention and a complementary fragrance compound as defined above. Still further, the fragrance formulation of the present invention comprises a compound of the present invention and a buffering agent as defined above.

The term "fragrance product" means a consumer product containing a fragrance ingredient that adds fragrance or masks malodor. Fragrance products may include, for example, perfumes, colognes, toilet water, personal care products, cleaning products, bar soaps, liquid soaps, shower gels, foam baths, cosmetic preparations, skin care products such as creams, lotions and shaving products, hair care products for shampooing, rinsing, conditioning, bleaching, coloring, dyeing and styling, deodorants and antiperspirants, feminine care products such as tampons and feminine napkins, baby care products such as diapers, bibs and wipes, family care products such as bath tissues, facial tissues, paper handkerchiefs or paper towels, fabric products such as fabric softeners and fresheners, air care products such as air fresheners and fragrance delivery systems, cleaning agents and disinfectants such as detergents, dishwashing materials, scrubbing compositions, glass and metal cleaners such as window cleaners, countertop cleaners, floor and carpet cleaners, toilet cleaners and bleach additives, washing agents such as all-purpose, heavy duty, and hand washing or fine fabric washing agents including laundry detergents and rinse additives, dental and oral hygiene products such as toothpastes, tooth gels, dental flosses, denture cleansers, denture adhesives, dentifrices, tooth whitening and mouthwashes, health care and nutritional products and food products such as snack and beverage products. The fragrance product of the present invention is a consumer product that contains a compound of the present invention. Further, the fragrance product of the present invention contains a compound of the present invention and a complementary fragrance compound as defined above. Still further, the fragrance product of the present invention comprises a compound of the present invention and a buffering agent as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

The term "a" or "an" is understood to mean one or more.

The term "olfactory acceptable amount" is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compound of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

The amount of the compounds of the present invention employed in a fragrance formulation varies from about $10^{-8}$ to about 70 weight percent, preferably from about $10^{-6}$ to about 50 weight percent, more preferably from about $10^{-4}$ to about 25 weight percent, and even more preferably from about 0.01 to about 10 weight percent. Those with skill in the art will be able to employ the desired amount to provide desired fragrance effect and intensity. In addition to the compounds of the present invention, other materials can also be used in conjunction with the fragrance formulation to encapsulate and/or deliver the fragrance. Some well-known materials are, for example, but not limited to, polymers, oligomers, other non-polymers such as surfactants, emulsifiers, lipids including fats, waxes and phospholipids, organic oils, mineral oils, petrolatum, natural oils, perfume fixatives, fibers, starches, sugars and solid surface materials such as zeolite and silica. Some preferred polymers include polyacrylate, polyurea, polyurethane, polyacrylamide, polyester, polyether, polyamide, poly(acrylate-co-acrylamide), starch, silica, gelatin and gum Arabic, alginate, chitosan, polylactide, poly(melamine-formaldehyde), poly(urea-formaldehyde), or a combination thereof.

When used in a fragrance formulation these ingredients provide additional notes to make a fragrance formulation more desirable and noticeable, and add the perception of value. The odor qualities found in these materials assist in beautifying and enhancing the finished accord as well as improving the performance of the other materials in the fragrance.

In addition, the compounds of the present invention are also surprisingly found to provide superior ingredient performance and possess unexpected advantages in malodor counteracting applications such as body perspiration, environmental odor such as mold and mildew, bathroom, etc. The compounds of the present invention substantially eliminate the perception of malodors and/or prevent the formation of such malodors, thus, can be utilized with a vast number of functional products.

Examples of the functional products are provided herein to illustrate the various aspects of the present invention. However, they do not intend to limit the scope of the present invention. The functional products may include, for example, a conventional room freshener (or deodorant) composition such as room freshener sprays, an aerosol or other spray, fragrance diffusers, a wick or other liquid system, or a solid, for instance candles or a wax base as in pomanders and plastics, powders as in sachets or dry sprays or gels, as in solid gel sticks, clothes deodorants as applied by washing machine applications such as in detergents, powders, liquids, whiteners or fabric softeners, fabric refreshers, linen sprays, closet blocks, closet aerosol sprays, or clothes storage areas or in dry cleaning to overcome residual solvent notes on clothes, bathroom accessories such as paper towels, bathroom tissues, sanitary napkins, towelettes, disposable wash cloths, disposable diapers, and diaper pail deodorants, cleansers such as disinfectants and toilet bowl cleaners, cosmetic products such as antiperspirant and deodorants, general body deodorants in the form of powders, aerosols, liquids or solid, or hair care products such as hair sprays, conditioners, rinses, hair colors and dyes, permanent waves, depilatories, hair straighteners, hair groom applications such as pomade, creams and lotions, medicated hair care products containing such ingredients as selenium sulphide, coal tar or salicylates, or shampoos, or foot care products such as foot powders, liquids or colognes, after shaves and body lotions, or soaps and synthetic detergents such as bars, liquids, foams or powders, odor control such as during manufacturing processes, such as in the textile finishing industry and the printing industry (inks and paper), effluent control such as in processes involved in pulping, stock yard and meat processing, sewage treatment, garbage bags, or garbage disposal, or in product odor control as in textile finished goods, rubber finished goods or car fresheners, agricultural and pet care products such as dog and hen house effluents and domestic animal and pet care products such as deodorants, shampoo or cleaning agents, or animal litter material and in large scale closed air systems such as auditoria, and subways and transport systems.

Thus, it will be seen that the formulation of the invention is usually one in which the malodor counteractant is present together with a carrier by means of which or from which the malodor counteractant can be introduced into air space wherein the malodor is present, or a substrate on which the malodor has deposited. For example, the carrier can be an aerosol propellant such as a chlorofluoro-methane, or a solid such as a wax, plastics material, rubber, inert powder or gel. In a wick-type air freshener, the carrier is a substantially odorless liquid of low volatility. In several applications, a formulation of the invention contains a surface active agent or a disinfectant, while in others, the malodor counteractant is present on a fibrous substrate. In many formulations of the invention there is also present a fragrance component which imparts a fragrance to the formulation. The fragrances stated above can all be employed.

Malodor counteracting effective amount is understood to mean the amount of the inventive malodor counteractant employed in a functional product that is organoleptically effective to abate a given malodor while reducing the combined intensity of the odor level, wherein the given malodor is present in air space or has deposited on a substrate. The exact amount of malodor counteractant agent employed may vary depending upon the type of malodor counteractant, the type of the carrier employed, and the level of malodor counteract capacity desired. In general, the amount of malodor counteractant agent present is the ordinary dosage required to obtain the desired result. Such dosage is known to the skilled practitioner in the art. In a preferred embodiment, when used in conjunction with malodorous solid or liquid functional products, e.g., soap and detergent, the compounds of the present invention may be present in an amount ranging from about 0.005 to about 50 weight percent, preferably from about 0.01 to about 20 weight percent, and more preferably from about 0.05 to about 5 weight percent, and when used in conjunction with malodorous gaseous functional products, the compounds of the present invention may be present in an amount ranging from about 0.1 to 10 mg per cubic meter of air.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, mL is understood to be milliliter, g is understood to be gram, Kg is understood to be kilogram, mol is understood to be mole, mmol is understood to be millimole, psi is understood to be pound-force per square inch, and mmHg be millimeters (mm) of mercury (Hg). IFF as used in the examples is understood to mean International Flavors & Fragrances Inc., New York, NY, USA.

Example I: Preparation of 5-(3,3-Dimethyloxiran-2-yl) 3-methylpentan-1-ol (Structure 1a)

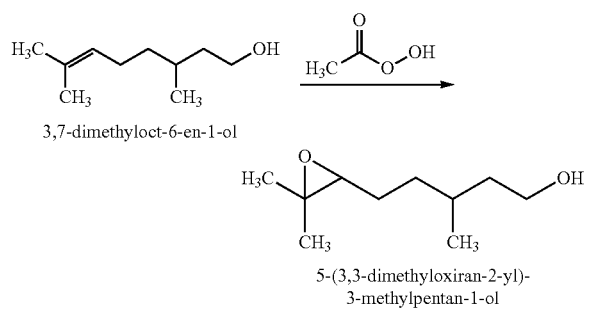

A mixture of 3,7-dimethyloct-6-en-1-ol (655 g, 3.98 mol) and sodium carbonate (Na$_2$CO$_3$) (150 g, 1.41 mol) was stirred in toluene (2 L) and cooled to 15° C. using an ice bath. To this mixture was added peracetic acid (CH$_3$COOOH) (32% in acetic acid) (994 g, 4.18 mol) over 3 hours while maintaining the temperature at 20-25° C. After the feed was complete, the reaction was aged at 25° C. for another 3 hours. The reaction mixture was washed sequentially with sodium carbonate solution (10%) (1 L), sodium sulfite solution (Na$_2$SO$_3$) (10%) (1 L) and brine solution (NaCl) (1 L) to afford a crude reaction mixture.

Example II: Preparation of 3,7-Dimethyloct-7-ene-1,6-diol (Structure 1b)

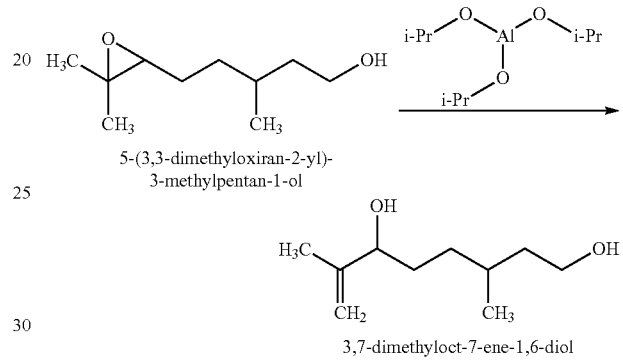

The crude reaction mixture from Example I was charged to a 3-L reaction flask fitted with a Dean-Stark trap that contained toluene (1 L) and heated to 120° C. Residual water was removed and the reaction mixture was cooled to room temperature. Aluminum isopropoxide (Al(O-i-Pr)$_3$) (70 g, 0.34 mol) was added and the reaction mixture was heated to reflux (125° C.) for 10 hours. The reaction mixture was then quenched with sodium hydroxide solution (NaOH) (15%) (1.35 Kg), washed with sodium hydroxide solution (10%) (1.2 Kg) followed by brine solution (1 L). The resulting mixture was distilled to afford 3,7-dimethyloct-7-ene-1,6-diol as a clear oil (679 g) having a boiling point of 152° C. at 1 mmHg.

$^1$H NMR (500 MHz, CDCl$_3$) δ: 4.87 (br s, 1H), 4.77 (br s, 1H), 3.93-4.00 (m, 1H), 3.51-3.68 (m, 2H), 2.75 (br s, 2H), 1.66 (s, 3H), 0.96-1.59 (m, 7H), 0.85 (d, J=6.6 Hz, 3H).

Example III: Preparation of 10-Hydroxy-4,8-dimethyldec-4-enal (Structure 1)

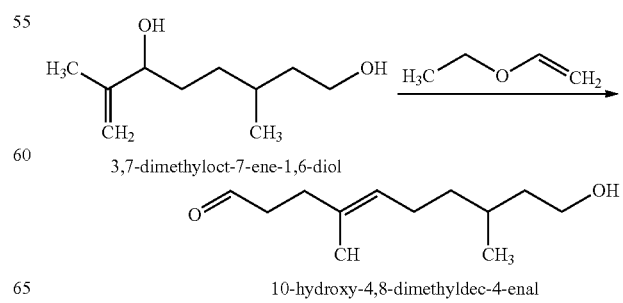

3,7-Dimethyloct-7-ene-1,6-diol (100 g, 0.58 mol) (obtained in Example II) was placed in a 1-L autoclave containing ethyl vinyl ether ($CH_3CH_2OCHF=C_2$) (209 g, 2.9 mol) and phenylphosphonic acid ($C_6H_5-PO(OH)_2$) (1.1 g, 0.007 mol). The autoclave was heated to 130° C. for 2 hours and then to 150° C. for additional 6 hours. The reaction mixture was worked up by adding hexanes (100 mL) and then washed with sodium bicarbonate solution ($NaHCO_3$) (200 mL) followed with brine solution (200 mL). The obtained crude product was distilled to afford 10-hydroxy-4,8-dimethyldec-4-enal (60 g) containing both (E)- and (Z)-isomers and having a boiling point of 195° C. at 2 mmHg.

(E)-10-hydroxy-4,8-dimethyldec-4-enal has the following NMR spectral characteristics: $^1$H NMR (500 MHz, $CDCl_3$) δ: 9.75 (t, J=2.05 Hz, 1H), 5.15 (m, 1H), 3.67 (m, 2H), 2.52 (m, 2H), 2.33 (m, 2H), 2.00 (m, 2H), 1.62 (s, 3H), 1.58 (m, 1H), 1.37 (m, 2H), 1.21 (m, 2H), 0.91 (d, J=6.6 Hz, 3H).

(Z)-10-hydroxy-4,8-dimethyldec-4-enal has the following NMR spectral characteristics: $^1$H NMR (500 MHz, $CDCl_3$) δ: 9.78 (t, J=1.93 Hz, 1H), 5.14 (m, 1H), 3.68 (m, 2H), 2.52 (m, 2H), 2.33 (m, 2H), 2.00 (m, 2H), 1.68 (s, 3H), 1.58 (m, 1H), 1.14-1.43 (m, 4H), 0.91 (d, J=6.6 Hz, 3H).

Example IV: Preparation of 10,10-Dimethoxy-3,7-dimethyldeca-1,6-diene

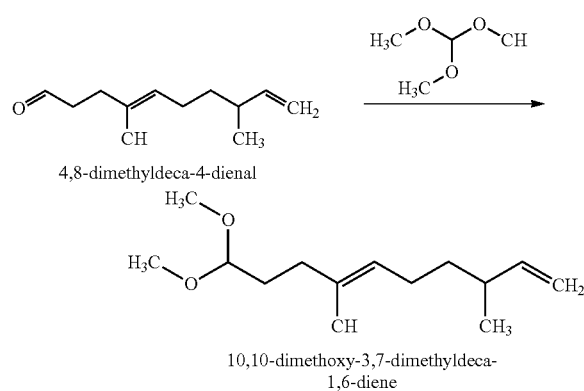

A mixture of 4,8-dimethyldeca-4,9-dienal (600 g, 3.3 mol), trimethyl orthoformate ($CH(OCH_3)_3$) (530 g, 5.0 mol) and methanol (60 mL) was charged to a 3-L round bottom flask equipped with a mechanical stirrer, a condenser and a thermocouple. The reaction mixture was cooled to 0-10° C. and hydrochloric acid solution (37%) (3 g, 0.03 mol) was added in one shot. The reaction mixture was allowed to exotherm to 20-30° C. and aged for 1 hour. After the reaction completed, which was confirmed by a gas chromatograph sample, the reaction mixture was quenched with sodium methoxide solution (25%) (20 g, 0.09 mol) and washed with brine solution (500 mL). The resulting mixture was distilled to afford 10,10-dimethoxy-3,7-dimethyldeca-1,6-diene (655 g) having a boiling point of 138° C. at 8 mmHg.

$^1$H NMR (400 MHz, $CDCl_3$) δ: 5.68 (ddd, J=17.3, 10.1, 7.5 Hz, 1H), 5.10-5.17 (m, 1H), 4.86-5.01 (m, 2H), 4.29-4.38 (m, 1H), 3.31 (s, 6H), 1.88-2.23 (m, 5H), 1.63-1.75 (m, 2H), 1.59 (s, 3H), 1.23-1.40 (m, 2H), 0.98 (d, J=6.8 Hz, 3H).

Example V: Preparation of 11,11-Dimethoxy-4,8-dimethylundec-7-enal

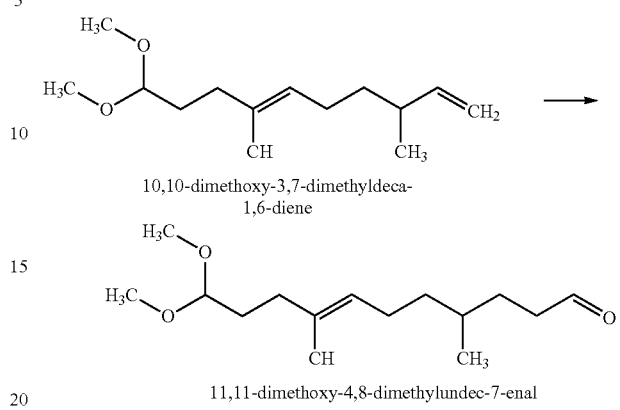

A mixture of 10,10-dimethoxy-3,7-dimethyldeca-1,6-diene (1.31 Kg, 5.8 mol) (obtained in Example IV), carbonyl hydrido tris(triphenylphosphine)rhodium(I) ([RhH(CO)(PPh_3)_3]) (Commercially available at Johnson Matthey Inc.) (4.5 g, 0.0049 mol), sodium bicarbonate (1.5 g, 0.018 mol) and toluene (300 mL) was charged to a 4-L autoclave, heated to 100° C. and pressurized with Syngas ($H_2$:CO ratio of 1:1) to 400 psi. The reaction mixture was aged for 8 hours. The resulting crude product of 11,11-dimethoxy-4,8-dimethylundec-7-enal was used directly in the next step.

$^1$H NMR (500 MHz, $CDCl_3$) δ: 9.70 (t, J=1.9 Hz, ~90% of 1H), 9.55-9.63 (m, 10% of 1H), 5.00-5.12 (m, 1H), 4.27 (t, J=5.7 Hz, 1H), 3.18-3.35 (m, 6H), 2.21-2.45 (m, 2H), 1.83-2.06 (m, 4H), 1.50-1.70 (m, 6H), 1.34-1.46 (m, 2H), 1.23-1.34 (m, 1H), 1.08-1.22 (m, 1H), 0.75-1.01 (m, 3H).

Example VI: Preparation of 11,11-Dimethoxy-4,8-dimethylundec-7-en-1-ol

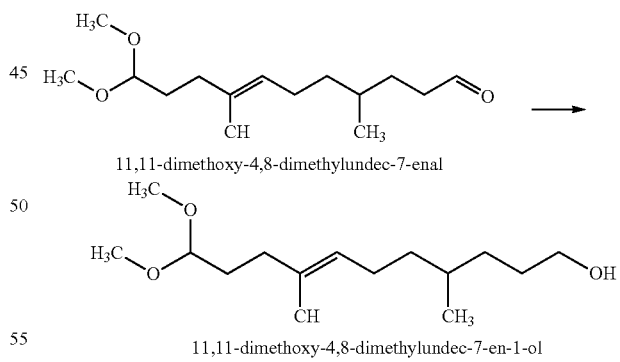

Sodium borohydride ($NaBH_4$) (20.5 g, 0.54 mol) and isopropyl alcohol ($CH_3CHOHCH_3$) (800 mL) was charged to a 3-L round bottom flask equipped with an addition funnel, a mechanical stirrer, a condenser and a thermocouple. The mixture was heated to 70° C. and 11,11-dimethoxy-4,8-dimethylundec-7-enal (612 g, 1.56 mol) (obtained in Example V) was fed in over 2 hours at 70-75° C. The reaction mixture was aged for 1 hour at 80° C. After the reaction completed, which was confirmed by a gas chromatograph sample, the reaction mixture was cooled, quenched with water, and washed with sodium hydroxide solution (10%) (500 mL) followed by two times of brine solution (500 mL). The crude product was distilled to afford 11,11-dimethoxy-4,8-dimethylundec-7-en-1-ol (404 g) with a boiling point of 163° C. at 6 mmHg.

$^1$H NMR (500 MHz, CDCl$_3$) δ: 5.09 (t, J=6.6 Hz, 1H), 4.29 (t, J=5.8 Hz, 1H), 3.50-3.61 (m, 2H), 3.27 (s, 6H), 1.83-2.05 (m, 4H), 1.59-1.71 (m, 2H), 1.56 (s, 3H), 1.42-1.56 (m, 2H), 1.24-1.41 (m, 3H), 1.01-1.23 (m, 2H), 0.84 (d, J=6.6 Hz, 3H).

Example VII: Preparation of
11-Hydroxy-4,8-dimethylundec-4-enal (Structure 2)

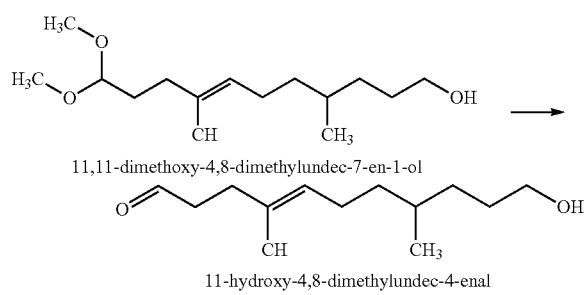

A mixture of 11,11-dimethoxy-4,8-dimethylundec-7(E/Z)-en-1-ol (260 g, 1.0 mols) (obtained in Example VI), trifluoroacetic acid (CF$_3$CO$_2$H) (14 g, 0.12 mol) (commercially available at Alfa Aesar), 2-butanone (CH$_3$C(O)CH$_2$CH$_3$) (650 g, 9.0 mol) and water (36 g, 2 mol) was charged to a 2-L round bottom flask equipped with a mechanical stirrer, a condenser and a thermocouple and heated to a gentle reflux at 73° C. and aged for 8 hours. The reaction mixture was then cooled, quenched with water (200 mL), and washed with sodium bicarbonate solution (3%) (200 mL). The resulting mixture was purified with Wiped Film Evaporation under a column temperature of 160° C. at 0.5 mmHg with a feed rate of 75 g/hour to afford 11-hydroxy-4,8-dimethylundec-4-enal (155 g).

$^1$H NMR (400 MHz, CDCl$_3$) δ: 9.60-9.90 (m, 1H), 5.03-5.30 (m, 1H), 4.52-4.60 (m, 4% of 1H), 4.35 (t, J=5.7 Hz, 13% of 1H), 3.63 (t, J=6.7 Hz, 2H), 3.30-3.33 (m, 13% of 6H), 2.45-2.57 (m, 2H), 2.27-2.41 (m, 2H), 1.88-2.15 (m, 2H), 1.62 (s, 3H), 1.26-1.62 (m, 5H), 1.08-1.24 (m, 2H), 0.89 (d, J=6.4 Hz, 3H).

Example VIII: Preparation of
12,12-Dimethoxy-5,9-dimethyldodec-8-en-2-ol

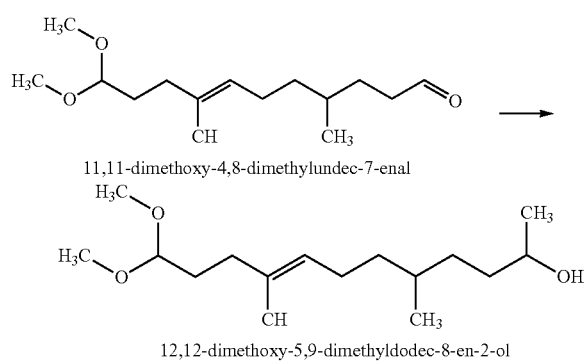

Methyl magnesium chloride solution (CH$_3$MgCl) in tetrahydrofuran (3M) (800 mL, 2.4 mol) was charged to a flame-dried 3-L round bottom flask equipped with an addition funnel, a mechanical stirrer, a condenser and a thermocouple and cooled to 10° C. 11,11-Dimethoxy-4,8-dimethylundec-7-enal (852 g, 2.16 mol) (obtained in Example V) was fed in over 3 hours at 10-15° C. The reaction mixture was aged for 1 hour at 20° C. After the reaction completed, which was confirmed by a gas chromatograph sample, the reaction mixture was quenched with ice (1 L) containing acetic acid (150 g, 2.5 mol), washed with brine solution (600 mL) followed by sodium carbonate solution (4%) (400 mL). The resulting mixture was distilled to afford 12,12-dimethoxy-5,9-dimethyldodec-8-en-2-ol (620 g) with a boiling point of 166° C. at 2 mmHg.

$^1$H NMR (500 MHz, CDCl$_3$) δ: 5.06-5.13 (m, 1H), 4.30 (t, J=5.7 Hz, 1H), 3.61-3.81 (m, 1H), 3.27 (s, 6H), 1.85-2.07 (m, 4H), 1.60-1.71 (m, 2H), 1.56 (s, 3H), 1.00-1.50 (m, 7H), 1.14 (d, J=6.2 Hz, 3H), 0.80-0.88 (m, 3H).

Example IX: Preparation of
11-Hydroxy-4,8-dimethyldodec-4-enal (Structure 3)

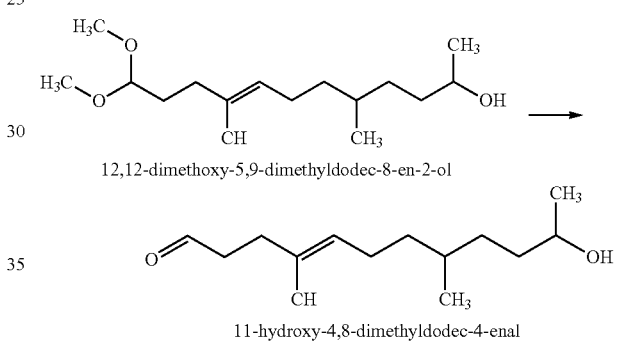

A mixture of 12,12-dimethoxy-5,9-dimethyldodec-8-en-2-ol (400 g, 1.4 mol) (obtained in Example VIII), trifluoroacetic acid (20 g, 0.175 mol), 2-butanone (1 Kg, 13.9 mol) and water (50 g, 2.8 mol) was charged to a 2-L round bottom flask equipped with a mechanical stirrer, a condenser and a thermocouple and heated to a gentle reflux at 73° C. and aged for 8 hours. The reaction mixture was then cooled, quenched with water (300 mL), and washed with sodium bicarbonate solution (3%) (300 mL). The resulting mixture was purified with Wiped Film Evaporation under a column temperature of 160° C. at 0.5 mmHg with a feed rate of 75 g/hour to afford of 11-hydroxy-4,8-dimethyldodec-4-enal (316 g).

$^1$H NMR (500 MHz, CDCl$_3$) δ: 9.61-9.76 (m, 1H), 5.00-5.18 (m, 1H), 4.53-4.62 (m, 3% of 1H), 4.27 (t, J=5.7 Hz, 1% of 1H), 3.58-3.79 (m, 1H), 3.23-3.27 (m, 1% of 6H), 2.37-2.51 (m, 2H), 2.19-2.34 (m, 2H), 1.79-2.00 (m, 2H), 1.55 (s, 3H), 0.97-1.50 (m, 7H), 1.11 (d, J=6.2 Hz, 3H), 0.75-0.86 (m, 3H).

Example X: Fragrance Evaluations

The above compounds of different concentrations ($10^{-4}$%, $10^{-3}$%, $10^{-2}$%, 0.1% and 1%) were evaluated for their fragrance properties at different pH values (2, 4, 5, 6, 7, 8, 9, 10, 11 and 12), wherein the pH was adjusted using a buffer of sodium (or potassium) citrate, sodium (or potassium) gluconate, sodium (or potassium) lactate, citric acid, monosodium citrate, gluconic acid, gluconolactone or lactic acid. The odor profiles at different pH values are reported in Table 2.

TABLE 2

| Compound | pH | | | |
|---|---|---|---|---|
| | 2 | 4 | 5-11 | 12 |
| Structure 1 | Off notes, plastic, very weak | Off notes, plastic, weak | Floral, sweet, juicy, green, watery | Off notes, solventy, green |
| Structure 2 | Off notes, fatty, very weak | Off notes, fatty, weak | Floral, diffusive, green, aldehydic | Burnt off notes, green, floral, weak |
| Structure 3 | Off notes, too aldehydic, very weak | Off notes, too aldehydic, weak | Floral, diffusive, green, aldehydic | Burnt off notes, green, floral, weak |

As shown above, Structures 1-3 exhibited desirable floral and green notes in a pH range of 5-11. Off-notes developed when the pH value was lower than 5 or higher than 11. Such odor profiles and advantageous properties in a specific pH range are unexpected.

Example XI: Analogs

In addition, the following analogs were prepared.

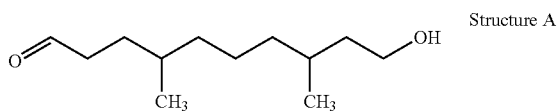

Structure A

Preparation of 10-Hydroxy-4,8-dimethyldecanal (Structure A)

10-Hydroxy-4,8-dimethyldecanal was prepared from Structure 1 (obtained in Example I-III) via selective hydrogenation.

$^1$H NMR (500 MHz, CDCl$_3$) δ: 9.74 (t, J=1.9 Hz, 1H), 3.58-3.69 (m, 2H), 2.33-2.46 (m, 2H), 1.47-1.76 (m, 3H), 1.15-1.46 (m, 7H), 1.01-1.15 (m, 2H), 0.80-0.90 (m, 6H).

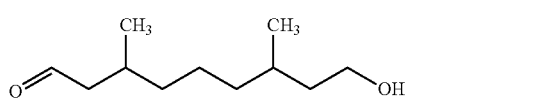

Structure B

Preparation of 9-Hydroxy-3,7-dimethylnonanal (Structure B)

9-Hydroxy-3,7-dimethylnonanal was prepared from 3,7-dimethyloctane-1,7-diol via a multi-step synthesis combining esterification, thermal cracking, base hydrolysis and hydroformylation.

$^1$H NMR (400 MHz, CDCl$_3$) δ: 9.71 (t, J=2.2 Hz, 1H), 4.57-4.67 (m, 8% of 1H), 3.55-3.70 (m, 2H), 2.30-2.41 (m, 1H), 2.15-2.25 (m, 1H), 1.97-2.07 (m, 1H), 1.48-1.61 (m, 2H), 1.02-1.39 (m, 8H), 0.92 (d, J=6.6 Hz, 3H), 0.85 (d, J=6.6 Hz, 3H).

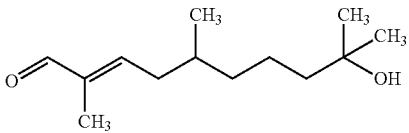

Structure C

Preparation of 9-Hydroxy-2,5,9-trimethyldec-2-enal (Structure C)

9-Hydroxy-2,5,9-trimethyldec-2-enal was prepared from hydroxycitronellal (commercially available at BASF) via aldol condensation.

$^1$H NMR (500 MHz, CDCl$_3$) δ: 9.31 (s, 1H), 6.42-6.47 (m, 1H), 2.23-2.31 (m, 1H), 2.08-2.18 (m, 1H), 1.65 (s, 3H), 1.57-1.67 (m, 1H), 1.23-1.40 (m, 5H), 1.13 (s, 6H), 1.09-1.20 (m, 1H), 0.86 (d, J=6.6 Hz, 3H).

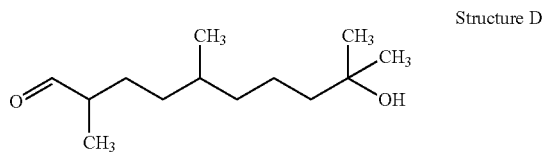

Structure D

Preparation of 9-Hydroxy-2,5,9-trimethyldecanal (Structure D)

9-Hydroxy-2,5,9-trimethyldecanal was prepared from hydroxycitronellal (commercially available at BASF) via aldol condensation followed by selective hydrogenation.

$^1$H NMR (500 MHz, CDCl$_3$) δ: 9.56-9.58 (m, 1H), 2.17-2.36 (m, 1H), 1.58-1.75 (m, 1H), 1.21-1.42 (m, 8H), 1.17 (s, 6H), 1.07-1.15 (m, 2H), 1.02-1.06 (m, 3H), 0.82-0.86 (m, 3H).

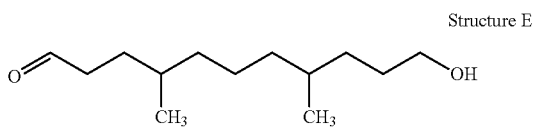

Structure E

Preparation of 11-Hydroxy-4,8-dimethylundecanal (Structure E

11-Hydroxy-4,8-dimethylundecanal was prepared from Structure 2 (obtained in Example IV-VII) via selective hydrogenation.

$^1$H NMR (400 MHz, CDCl$_3$) δ: 9.77 (t, J=1.9 Hz, 1H), 3.63 (t, J=6.7 Hz, 2H), 2.34-2.51 (m, 2H), 1.49-1.78 (m, 3H), 1.21-1.49 (m, 8H), (m, 3H), 0.84-0.96 (m, 6H).

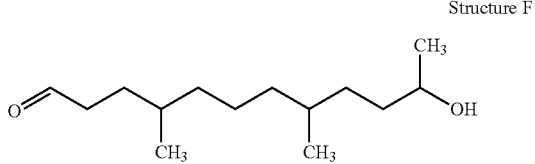 [SMILES: CC(O)CCC(C)CCCC(C)CCC=O]

Structure F

Preparation of 11-Hydroxy-4,8-dimethyldodecanal (Structure F)

11-Hydroxy-4,8-dimethyldodecanal was prepared from Structure 3 (obtained in Example IV, V, VIII and IX) via selective hydrogenation.

$^1$H NMR (600 MHz, CDCl$_3$) δ: 9.77 (t, J=1.9 Hz, 1H), 3.71-3.81 (m, 1H), 2.37-2.48 (m, 2H), 1.62-1.72 (m, 1H), 1.21-1.54 (m, 10H), 1.16-1.20 (m, 3H), 1.04-1.16 (m, 3H), 0.83-0.91 (m, 6H).

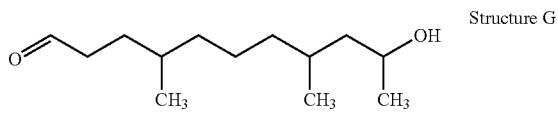

Structure G

Preparation of 10-Hydroxy-4,8-dimethylundecanal (Structure G)

10-Hydroxy-4,8-dimethylundecanal was prepared from Citronellal via a multi-step synthesis combining a methyl Grignard reaction, an epoxidation with peracetic acid, a rearrangement of the epoxide to an allylic alcohol and a Claisen rearrangement with butyl vinyl ether.

$^1$H NMR (500 MHz, CDCl$_3$) δ: 9.68-9.78 (m, 1H), 3.82-3.89 (m, 1H), 2.33-2.45 (m, 2H), 1.47-1.67 (m, 2H), 0.99-1.47 (m, 13H), 0.78-0.92 (m, 6H).

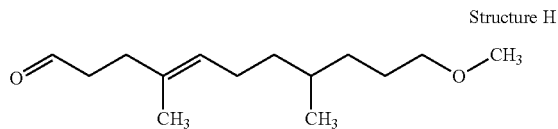 [SMILES: COCCCC(C)CC/C=C(\C)CCC=O]

Structure H

Preparation of 11-methoxy-4,8-dimethylundec-4-enal (Structure H)

11-Methoxy-4,8-dimethylundec-4-enal was prepared from Structure 2 (obtained in Example IV-VII) via a multi-step synthesis combining an initial protecting step to form the cyclic acetal, followed by hydrogenation and conversion to methyl ether, and a final de-protection step.

$^1$H NMR (500 MHz, CDCl$_3$) δ: 9.73-9.76 (m, 1H), 5.11-5.17 (m, 1H), 3.34 (t, J=6.9 Hz, 2H), 3.32 (s, 3H), 2.45-2.54 (m, 2H), 2.26-2.36 (m, 2H), 1.84-2.17 (m, 2H), 1.45-1.77 (m, 5H), 1.22-1.44 (m, 3H), 1.03-1.21 (m, 2H), 0.81-0.93 (m, 3H).

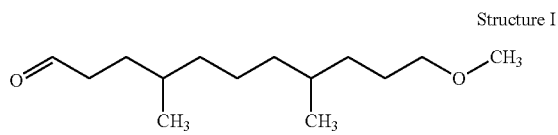 [SMILES: COCCCC(C)CCCC(C)CCC=O]

Structure I

Preparation of 11-Methoxy-4,8-dimethylundecanal (Structure I)

11-Methoxy-4,8-dimethylundecanal was prepared from Structure 2 (obtained in Example IV-VII) via a multi-step synthesis combining an initial protecting step to form the cyclic acetal, followed by hydrogenation and conversion to methyl ether, and a final de-protection step.

$^1$H NMR (500 MHz, CDCl$_3$) δ: 9.75 (t, J=1.9 Hz, 1H), 3.33 (t, J=6.6 Hz, 2H), 3.31 (s, 3H), 2.33-2.46 (m, 2H), 1.47-1.71 (m, 3H), 1.17-1.46 (m, 8H), 1.00-1.17 (m, 3H), 0.81-0.89 (m, 6H).

When compared with Structure A-I, Structures 1-3 exhibited unique and highly desirable floral, sweet, juicy, green and lily of the valley notes, which were lacking in Structures A-I. Further, such notes were strong and long-lasting. Such advantageous properties are unexpected.

What is claimed is:

1. A compound selected from the group consisting of 11-hydroxy-4,8-dimethyldodec-4-enal; 10-hydroxy-4,8-dimethylundec-4-enal; and a mixture thereof.

2. A fragrance formulation comprising an olfactory acceptable amount of a compound selected from the group consisting of 11-hydroxy-4,8-dimethyldodec-4-enal; 10-hydroxy-4,8-dimethylundec-4-enal; and a mixture thereof; and a buffering agent; wherein the fragrance formulation has a pH range of from 5 to 11.

3. The fragrance formulation of claim 2, wherein the olfactory acceptable amount is from about $10^{-6}$ to about 50 weight percent of the fragrance formulation.

4. The fragrance formulation of claim 2, wherein the olfactory acceptable amount is from about $10^{-4}$ to about 25 weight percent of the fragrance formulation.

5. The fragrance formulation of claim 2, wherein the olfactory acceptable amount is from about 0.01 to about 10 weight percent of the fragrance formulation.

6. The fragrance formulation of claim 2 further comprising a polymer.

7. The fragrance formulation of claim 6, wherein the polymer is selected from the group consisting of polyacrylate, polyurea, polyurethane, polyacrylamide, polyester, polyether, polyamide, poly(acrylate-co-acrylamide), starch, silica, gelatin and gum Arabic, alginate, chitosan, polylactide, poly(melamine-formaldehyde), poly(urea-formaldehyde) and a combination thereof.

8. The fragrance formulation of claim 2, wherein the buffering agent is selected from the group consisting of an acetate buffer, an alkylamine buffer, an aminoethyl alcohol buffer, an ammonium buffer, an arginine buffer, a barbiturate buffer, a borate buffer, a carbonate buffer, a citrate buffer, an ethylenediamine buffer, a gluconate buffer, a glutamate buffer, a glycine buffer, a glycyl glycine buffer, an imidazole buffer, a lactate buffer, a malate buffer, a phosphate buffer, a pyridine buffer, a tartrate buffer, a tris buffer, a triethanolamine buffer, and a mixture thereof.

9. A method of improving, enhancing or modifying a fragrance formulation comprising the step of adding to the fragrance formulation an olfactory acceptable amount of a compound selected from the group consisting of 11-hydroxy-4,8-dimethyldodec-4-enal; 10-hydroxy-4,8-dimethylundec-4-enal; and a mixture thereof; and a buffering agent; wherein the fragrance formulation has a pH range of from 5 to 11.

10. The method of claim 9, wherein the olfactory acceptable amount is from about 10-6 to about 50 weight percent of the fragrance formulation.

11. The method of claim 9, wherein the olfactory acceptable amount is from about 10"4 to about 25 weight percent of the fragrance formulation.

12. The method of claim 9, wherein the olfactory acceptable amount is from about 0.01 to about 10 weight percent of the fragrance formulation.

13. A fragrance product containing the compound of claim 1.

14. The fragrance product of claim 13, wherein the fragrance product is selected from the group consisting of a perfume, a cologne, toilet water, a personal care product, a cleaning product, a bar soap, a liquid soap, a shower gel, a foam bath, a cosmetic preparation, a skin care product, a hair care product, a deodorant, an antiperspirant, a feminine care product, a baby care product, a family care product, a fabric product, an air care product, a fragrance delivery system, a cleaning agent, a disinfectant, a washing agent, a dental and oral hygiene product, a health care and nutritional product and a food product.

15. The fragrance product of claim 14, wherein the cleaning product is selected from the group consisting of a detergent, a dishwashing material, a scrubbing composition, a glass cleaner, a metal cleaner, a countertop cleaner, a floor cleaner, a carpet cleaner, a toilet cleaner and a bleach additive.

16. The fragrance product of claim 14, wherein the washing agent is selected from the group consisting of a laundry detergent and a rinse additive.

\* \* \* \* \*